United States Patent [19]
Cullis-Hill

[11] Patent Number: 5,514,667
[45] Date of Patent: May 7, 1996

[54] METHOD FOR TOPICAL TREATMENT OF HERPES INFECTIONS

[75] Inventor: David Cullis-Hill, Bondi Junction, Australia

[73] Assignee: Arthropharm Pty. Limited, Bondi Junction, Australia

[21] Appl. No.: 508,788

[22] Filed: Jul. 28, 1995

Related U.S. Application Data

[63] Continuation of Ser. No. 84,324, Jun. 30, 1993, abandoned, which is a continuation of Ser. No. 786,880, Nov. 5, 1991, abandoned.

[30] Foreign Application Priority Data

Nov. 5, 1990 [AU] Australia .................................. PK3174

[51] Int. Cl.⁶ .................................................. A61K 31/715
[52] U.S. Cl. .............................. 514/54; 514/26; 514/56; 514/59; 514/159; 514/165; 514/169; 514/177; 514/458; 514/728
[58] Field of Search ................................ 514/26, 54, 56, 514/59, 159, 165, 169, 177, 458, 728

[56] References Cited

U.S. PATENT DOCUMENTS

| | | | |
|---|---|---|---|
| 4,900,815 | 2/1990 | Tanaka et al. | 536/54 |
| 5,055,301 | 10/1991 | Voigt et al. | 424/422 |
| 5,055,457 | 10/1991 | Schrinner et al. | 514/59 |
| 5,100,879 | 3/1992 | Ueno et al. | 514/59 |
| 5,145,841 | 9/1992 | Cullis-Hill et al. | 515/54 |
| 5,153,181 | 10/1992 | Diringer et al. | 514/54 |
| 5,158,940 | 10/1992 | LaRocca et al. | 514/54 |

FOREIGN PATENT DOCUMENTS

| | | |
|---|---|---|
| 0746855 | 8/1970 | Belgium. |
| 0114589 | 8/1984 | European Pat. Off.. |
| 0596240 | 3/1978 | U.S.S.R.. |
| 0731967 | 5/1980 | U.S.S.R.. |
| 1050708 | 10/1983 | U.S.S.R.. |
| 2080682 | 2/1982 | United Kingdom. |

OTHER PUBLICATIONS

"Principles of Medicinal Chemistry", third edition, W. O. Foye, ed., Lea and Febiger, Philadelphia, 1989, Chapter 23.
Kobayashi et al; Tokushima J. Exp. Med. 26:41–51 (1979).
Yamashita et al; Dev. Oncor. 4 (Metasis):127–131 (1980).
Maat et al; J. Cancer Res. Clin. Oncol. 101:275–283 (1981).
Folkman et al; Science 221:719–725 (1983).
Gorelik et al; Int. J. Cancer 33:87–94 (1984).
Milas et al; Clin. Expl. Metastasis 3(4):247–255 (1985).
Spruance et al; Antmicrob. Agents Chemother. 30(1):196–B (Jul. 1986).
Goodman and Gilman's 7th Ed. pp. 1471–1472 2nd 594.
*The Merck Manual 15th ed. (1987) pp. 158–171, 180–1.*
Sakamoto et al; Invasion Metastasis 7:208–216 (1987).
Gorelik; Cancer Res. 47:809–815 (Feb. 1987).
Coombe et al; Int. J. Cancer 39(1):82–88 (1987).
Nakashima et al; JPN. J. Cancer Res. 78:1164–1168 (1987).
Van Gendersen et al; Chem. AB. 108:15849f (1988).
Kristofferson et al; J. Gen. Virol. 69(6):1157 . 1166 (1988).
Yamamoto et al; Chem. AB 111:167383z (1989).
Oeberg: Chem. AB. 110:878032 (1989).
Ito et al; Eur. J. Clin. Microbiol. Infect. Dis. 8:171–173 (1989).
Folkman et al; Science 243:1490–1493 (1989).
Dillman et al; Mol. Brother. 4:117–121 (1992).
Parish et al "Evidence that Sulphated . . . " Int. J. Cancer 40:511–8 (1987).
Baba et al "Sulphated Polysaccharides Are . . . " Antmicrob. Agents Chemother. 32:1742–5 (1988).
Czekelius—Abstract, p. 79 I. Abt. Orig. A217 (1971):300–325.
Schramm-Thiel et al—Abstract, p. 79 Arzneim.–Forsch.21(a) (1971):1389–1392.
Raff et al—Abstract pp. 79–80.
Münch. Med. WSCHR. 119 Nr. 25 (1977):817–818.

*Primary Examiner*—Douglas W. Robinson
*Assistant Examiner*—Kathleen Kahler Fonda
*Attorney, Agent, or Firm*—Nixon & Vanderhye

[57] ABSTRACT

A method for the topical treatment of herpes virus infections of the skin and mucous membranes is disclosed- This method uses a topical preparation comprising an anti-vital drug in combination with a potentiating drug which is an anti-inflammatory or an anti-oxidant drug. A preferred preparation includes zinc pentosan polysulphate in combination with bufexamac.

7 Claims, No Drawings

METHOD FOR TOPICAL TREATMENT OF HERPES INFECTIONS

This is a Rule 62 Continuation of application Ser. No. 08/084,324, filed 30 June 1993, now abandoned, which is a continuation of application Ser. No. 07/786,880, filed 5 November 1991, now abandoned.

FIELD OF THE INVENTION

This invention relates to therapeutic compositions for the topical treatment of vital conditions and neoplastic disorders, in particular to a composition in topical form comprising an anti-vital or an anti-neoplastic drug in combination with a potentiating drug which is an anti-inflammatory or an anti-oxidant drug.

BACKGROUND OF THE INVENTION

Topical drug treatments of virat conditions such as herpes simplex and neoplastic disorders such as carcinoma of the skin have been used for many years with only a moderate degree of success.

A number of drugs which demonstrate anti-vital activity in-vitro and when used systemically, surprisingly do not show efficacy when used topically. Examples of such drugs are sulphated polysaccharides as described by Parish et al, Inst. J. Cancer, 40, 511–518 (1987), particularly dextran sulphate, pentosan polysulphate, Eucoidan and carrageenins Baba et al, Antimicrobial Agents and Chemotherapy, 32, 1742–1748 (1988) specifically disclose that these compounds were found when tested in-vitro to be potent inhibitors for herpes simplex virus, human cytomegalovirus, visicular stomatitis virus, Sindbis virus and human immunodeficiency virus. They were also found to be moderately inhibitory to vaccinia virus but not inhibitory to adeno virus, coxsackie virus, polio virus, para-influenza virus and reo virus.

Sodium pentosan polysulphate (SP54) has also been shown by Raff et al, Munch. Med. Wschr., 119, 23, 817–818 (1977) to have potent anti-vital activity both in-vitro and when given intramuscularly in the treatment of herpes zoster.

Other drugs falling within the scope of this group which exhibit in-vitro and systemic anti-viral activity include foscarnet, suramin, polysutphated polysaccharides, polysulphated polymers, purine nucleoside analogues and derivatives thereof.

Elsewhere, in U.S. Pat. No. 4,710,493 (Landsberger) are disclosed compositions comprising in combination a glycosoaminoglycan polysulphate (excluding heparin) and a cytotoxic drug. The known serious side effects of the cytotoxic drug were found to be considerably reduced by this combination.

SUMMARY OF THE INVENTION

The present inventor has found that although the aforementioned drugs are essentially ineffective in the topical treatment of viral conditions and neoplastic disorders, surprisingly the combination of one of these drugs with an anti-inflammatory or anti-oxidant drug results in the potentiation of the first mentioned drug, thereby providing an effective topical treatment for these conditions and disorders.

This finding is particularly surprising given that a topical formulation comprising a pentosan polysulphate in combination with ethylene glycol monosalicylate ester has been sold for a number of years for the treatment of musculoskeletal disorders.

It is still further surprising given that when either of the drugs are used separately in topical form, they are essentially inactive.

Accordingly, the present invention consists in a method for the topical treatment of vital conditions or neoplastic disorders comprising applying an effective amount of a composition which includes a first compound selected from the group consisting of loscarnet, suramin, sulphated polysaccharides, polysulphated polysaccharides, polysulphated polymers, purine nucleoside analogues and derivatives thereof, and an amount of an anti-inflammatory or anti-oxidant drug sufficient to potentiate the activity of the first compound, to an area of the skin or mucous membranes affected by a viral condition or neoplastic disorder.

DESCRIPTION OF THE INVENTION

It is preferred that the first compound is selected from the group consisting of loscarnet, suramin, sulphated polysaccharides such as heparin and polysulphated saccharides such as dextran polysulphate, pentosan polysulphate, mannose polysulphate, carageenan and fucoidan and monovalent and polyalent salts and complexes thereof. Preferred anti-inflammatory drugs are selected from non-steroidal and steroidal groups of drugs with the anti-oxidant drug being selected from carotenoids, vitamin E, vitamin A, retinoic acid and retinol and derivatives thereof.

Amongst the non-steroidal anti-inflammatory group of drugs that may be used are salicylate derivatives and compounds such as diclofenac, naproxen and bufexamac.

More preferably the anti-virat and/or anti-neoplastic compound is a polysulphated polysaccharide in the form of monovalent or polyvalent salts and complexes, of molecular weight between about 1,000 and 30,000 Daltons and in a concentration of from 0.01 to 20 weight percent. These monovalent or polyvalent salts and complexes are disclosed in the present applicant's patent application WO88/07060, the contents of which are incorporated herein. More specifically, the compound is a divalent metal ion chelate of a polysulphate of xylan having glycosidically linked D-glucuronyl side chains with divalent metal ions chelated thereto in which the monovalent ions have been substituted by divalent metal ions selected from calcium, magnesium, copper and zinc ions. Magnesium complexes and zinc complexes of polysulphated polysaccharide are preferred as both magnesium and zinc are known to assist in wound healing.

Generally in the compositions of the invention, the anti-inflammatory drug or anti-oxidant drug will be incorporated in an amount of about 0.01 to about 50 weight percent.

Most preferably the anti-vital and anti-neoplastic compound is pentosan polysulphate of a molecular weight about 6,000 Daltons in a concentration of about 0.5 weight percent whilst the anti-inflammatory drug is triethanolamine salicylate in a concentration of about 10 weight percent or bufexamac in a concentration of about 1 weight %.

Particularly preferred is the zinc complex of pentosan polysulphate in combination with bufexamac.

The compositions of the invention will be formulated using pharmaceutical bases suitable to the site of application and may include dosage forms such as creams, ointments, lotions and the like. A person of skill in this art could readily formulate suitable such compositions.

In order to better understand and appreciate the nature of this invention, a number of examples will now be described.

EXAMPLE 1

0.5g of zinc pentosan polysulphate and 10 ml of triethanolamine salicylate was mixed with 90 ml of sorbolene cream.

This formulation was applied topically to a patient with the following clinical history. Extensive superficial herpes errosions to the skin resistant to conventional therapy. A formulation containing zinc pentosan polysulphate was applied with no effect. Viral culture indicated that the virus was resistant to a number of agents but was sensitive to loscarnet, which was administered for 2 weeks by in,ravenous infusion. One week after the cessation of the foscarnet therapy the lesions re-occurred. The lesion was then treated with the mixture of zinc pentosan polysulphate and triethanolamine salicylate in a cream base. Two days after treating the lesions with the mixture the lesions healed and have remained absent for a period of 3 months.

EXAMPLE 2

Zinc pentosan polysulphate at a concentration of 0.5% and sodium pentosan polysulphate at a concentration of 4% was compared to 0.5% zinc pentosan polysulphate mixed with 10% triethanolamine salicylate.

Five patients were treated with each formulation twice daily on the lesions. Only the group receiving the zinc pentosan polysulphate mixed with triethanolamine salicylate, showed alteration of the course of the lesions, and were essentially asymptomatic at 48 hours after start of treatment.

EXAMPLE 3

Four cases of chronic herpes simplex of five or more years duration of the lip were treated with sodium pentosan polysulphate (0.5%) combined with ethylene glycol monosalicylate ester (10%) in a cream base. All cases resolved within 2–5 days and no further outbreaks in that area of skin have occurred over the proceeding 12 months.

EXAMPLE 4

Early skin carcinoma characterised by toughening of the skin on the skull of a 60 year old male, which had previously been treated with cryosurgery, were treated twice daily with a 0.5% pentosan polysulphate and 10% ethylene glycol monosalicylate ester in a cream base. The lesions resolved and have remained clear for 12 months.

EXAMPLE 5

10 cases of herpes simplex were treated with a cream comprising 1 weight percent bufexamac and 0.5 weight percent zinc pentosan polysulphate.

The results achieved were comparable to those achieved in Example 2 in which triethanolamine salicylate 10% was used in place of bufexamac 1%.

It will be seen from these Examples that this invention provides effective treatment of a number of topical vital and neoplastic disorders. The treatments may be readily administered given that the compositions used for the treatment are in dosage forms such as creams, ointments and lotions.

Whilst this invention has been described with reference to the Examples and certain preferred embodiments, it will be appreciated by those skilled in the art that numerous variations and modifications are possible without departing from the spirit or scope thereof as broadly described.

I claim:

1. A method for the topical treatment of herpes infections in humans, comprising the step of applying to an area of skin or mucous membranes infected with herpes an effective amount of a composition which comprises a first compound which is a divalent metal ion chelate of a polysulphate of xylan having glycosidically linked D-glucuronyl side chains with divalent metal ions chelated thereto wherein the monovalent ions have been substituted by divalent ions selected from the group consisting of $Ca^{2+}$, $Mg^{2+}$, $Cu^{2+}$ and $Zn^{2+}$ in a concentration of 0.01 to about 20 weight percent, and a second compound which is a non-steroidal anti-inflammatory drug in a concentration of from about 0.01 to about 50 weight percent based on the total weight of the composition.

2. A method as in claim 1, wherein the non-steroidal anti-inflammatory drug is selected from the group consisting of diclofenac, naproxen, salicylate derivatives and bufexamac.

3. A method for the topical treatment of herpes infection in humans, comprising the step of applying to an area of the skin or mucous membranes infected with herpes an effective amount of a composition which comprises a divalent metal ion chelate of a polysulphate of xylan having glycosidically linked D-glucuronyl side chains with divalent metal ions chelated thereto wherein the monovalent ions have been substituted by divalent ions selected from the group consisting of $Ca^{2+}$, $Mg^{2+}$, $Cu^{2+}$ and $Zn^{2+}$ in a concentration of from 0.01 to about 20 weight percent based on the total weight of the composition, and a non-steroidal anti-inflammatory drug selected from the group consisting of diclofenac, naproxen, salicylate derivatives and bufexamac in a concentration of from about 0.01 to about 50 weight percent based on the total weight of the composition.

4. A method as in claim 3, wherein the divalent metal ion is zinc or magnesium.

5. A method as in claim 4, wherein the composition comprises the zinc chelate or the magnesium chelate of said polysulphate of xylan of molecular weight about 6,000 Daltons in a concentration of about 0.5 weight percent based on the total weight of the composition, and triethanolamine salicylate in a concentration of about 10 weight percent based on the total weight of the composition, or bufexamac in a concentration of about 1 weight percent based on the total weight of the composition.

6. A method as in claim 5, wherein the composition comprises about 0.5 weight percent based on the total weight of the composition of the zinc complex of said polysulphate of xylan and about 1 weight percent of bufexamac based on the total weight of the composition.

7. A method as in claim 6, wherein the herpes infection is a herpes simplex infection.

* * * * *